United States Patent [19]

Buchan et al.

[11] Patent Number: 4,688,562

[45] Date of Patent: Aug. 25, 1987

[54] MEDICAL DEVICE, ITS PREPARATION AND USE

[75] Inventors: Ian A. Buchan, Mountfitchet; Richard D. Heath, Dunmow, both of United Kingdom

[73] Assignee: Smith and Nephew Associated Companies, p.l.c., United Kingdom

[21] Appl. No.: 772,637

[22] Filed: Sep. 5, 1985

[30] Foreign Application Priority Data

Sep. 5, 1984 [GB] United Kingdom ............... 8422467
Sep. 7, 1984 [GB] United Kingdom ............... 8422706

[51] Int. Cl.$^4$ ............................................. A61F 5/46
[52] U.S. Cl. ................................ 128/132 R; 128/153
[58] Field of Search ............... 128/132 R, 149, 156, 128/153; 5/451

[56] References Cited

U.S. PATENT DOCUMENTS

| | | | |
|---|---|---|---|
| Re. 31,887 | 5/1985 | Hodgson | 128/132 R |
| 852,328 | 4/1907 | Hasselman et al. | 128/153 |
| 2,583,652 | 1/1952 | Keagy | 128/153 |
| 3,020,910 | 2/1962 | Ward | 128/132 R |
| 4,456,642 | 6/1984 | Burgdorfer et al. | 428/68 |
| 4,516,571 | 5/1985 | Buchan | 128/156 |

*Primary Examiner*—E. Rollins Cross
*Attorney, Agent, or Firm*—Jacobs & Jacobs

[57] ABSTRACT

A device for the prophylaxis of pressure sores which comprises a liquid retained within a flexible elastomeric envelope is described. The body contacting surface of the device is a film which has a moisture vapor transmission rate of greater than 300 g/m$^2$/24 hr at 37° C. at 100% to 10% relative humidity difference. The liquid is a viscous liquid which absorbs moisture vapor. The device is formed in the shape of the letter "U" which makes the device particularly useful for application to the sacrum. A device in which the liquid retained within the flexible envelope is a mixture of a viscous liquid and a hygroscopic material is also described.

20 Claims, 1 Drawing Figure

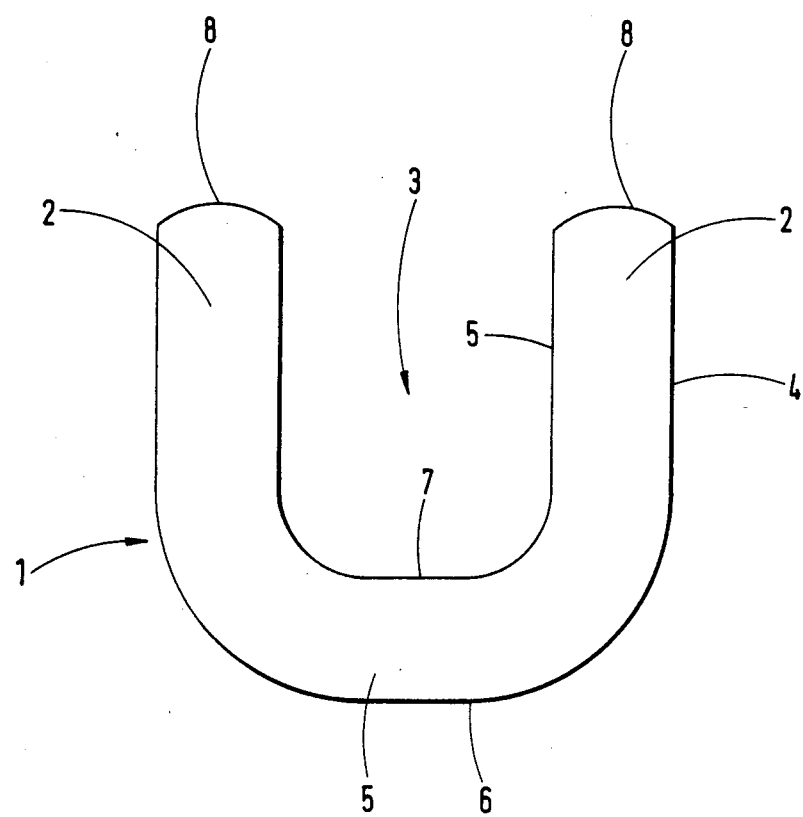

MEDICAL DEVICE, ITS PREPARATION AND USE

The present invention relates to devices for application to the pressure bearing surfaces of, for example, bedridden patients for the prophylaxis of pressure sores. In one particular aspect it relates to devices which comprise a viscous liquid containing a hygroscopic material retained within a flexible, elastomeric envelope. In a second particular aspect it relates to specially shaped devices for use on the sacrum. The present invention also relates to methods of forming such devices and to their use in pressure sore prophylaxis.

A prophylactic device for pressure sores consisting of a cross-linked water insoluble immobile polyurethane gel contained within an outer envelope has been described in U.S. Pat. No. 4,456,642. The prophylactic device described therein is adapted to be used as a cushion or a mattress and as such only provides protection to the patient when the patient is actually in position on the prophylactic device. If the patient is moved from where he is on the prophylactic device then he will no longer be afforded protection. U.S. Pat. No. 4,516,571 describes a prophylactic device which is removably attached to the body and which comprises a mobile moisture absorbing hydrophilic gel retained within a flexible elastomeric envelope. The device is adapted to move with the patient and indeed may be adhered to the patient for up to seven days or more. For this reason the envelope's body contacting surface is a film which has a moisture vapour transmission rate of greater than 300 g/m$^2$/24 hr at 37° C. at 100% to 10% relative humidity difference so that the risk of maceration and degeneration of the underlying skin is avoided.

In an aspect of the invention the flexible elastomeric envelope is adapted to provide the device within a special shape. It has been found that the known pressure sore prophylactic devices, when applied to certain parts of the body such as the sacrum, have not provided the decrease in pressure on the load bearing surfaces expected or have redistributed the pressure to occasion load stressed areas elsewhere thereby causing a pressure sore. This has been true of devices applied to the sacrum. It has been found that such disadvantages are mitigated if the device is in the shape of the letter "U".

Accordingly the present invention provides a device for the prophylaxis of pressure sores which comprises a liquid retained within a flexible elastomeric envelope in which the body contacting surface of the device is a film having a moisture vapour transmission rate of greater than 300 gm$^{-2}$24 hr$^{-1}$ at 37° C. at 100% to 10% relative humidity difference and the liquid is viscous and absorbs moisture vapour characterised in that the flexible elastomeric envelope is formed in the shape of the letter "U".

It is intended that where the flexible elastomeric envelope of the device of this invention is described as being in the shape of the letter "U", this description shall also include flexible elastomeric envelopes in the shape of the letter "C", a horseshoe and flexible elastomeric envelopes in the shape of an interrupted circle.

Suitably the flexible elastomeric envelope of the device is in the shape of the letter "U" which flexible elastomeric envelope is suitably between 5 cm and 30 cm long and preferably 10 cm to 20 cm long, when measured from the ends of the "arms" to the "base" of the flexible elastomeric envelope of the device, and which is suitably between 5 cm and 40 cm wide and preferably between 12 cm and 26 cm wide, when measured between the outer faces of the two "arms" of the flexible elastomeric envelope of the device. Each "arm" of the flexible elastomeric envelope of the device is suitably between 1 cm and 10 cm wide and preferably between 2 cm and 6 cm wide when measured between the "outer" and "inner" face of each arm. The two "arms" of the flexible elastomeric envelope of the device are separated by a gap which has a width of between 1 cm and 10 cm and preferably a width of between 2 cm and 6 cm.

The "base" of the flexible elastomeric envelope of the device is suitably between 2 cm and 25 cm wide and preferably between 5 cm and to 15 cm wide when measured between the "inner" and "outer" face of the base.

The thickness of the viscous moisture absorbing liquid filled flexible elastomeric envelope will be suitably between 0.5 cm and 3 cm and preferably between 1 cm and 2 cm. When reference is made to the parts of the flexible elastomeric envelope being described as "arm", "base", "outer" and "inner" it is intended that such reference should be the same as the references in the description of the drawing of this application.

When reference is made to moisture vapour transmission rate, it is intended that such measurements are carried out by the Payne Cup method which is described in the Description.

Suitably the moisture absorbing viscous liquid will be a material which is a viscous liquid and which will absorbe moisture vapour. Suitable materials which are moisture absorbing viscous liquids include polyurethanes, polyethylene glycols, propylene glycols, polyoxyethylene polyoxypropylene diol block copolymers which have the correct viscosity characteristics and are capable of deforming so as to distribute an applied pressure more or less evenly over their surface. Suitable polyurethane moisture absorbing viscous liquids include those hydrophilic polyurethane gels described in International Application No. WO 82/01306 and European Patent Application No. 122035 which are incorporated hereinafter by cross reference.

It is also envisaged that the moisture absorbing viscous liquid could comprise a viscous liquid which contained a hygroscopic material as described above.

It has now been found that by including a separate hygroscopic material in the viscous liquid retained within the flexible, elastomeric envelope a device is formed which may have an increased absorptive capacity for moisture and an increased absorption rate. Also the use of a separate hygroscopic material can permit the use of cheaper viscous liquids than the specialised hydrophilic polymers hitherto used.

Accordingly the present invention provides a device for the prophylaxis of pressure sores which comprises a liquid retained within a flexible, elastomeric envelope in which the body contacting surface of the device is a film having a moisture vapour transmission rate of greater than 300 gm$^{-2}$24 hr$^{-1}$ at 37° C. at 100% to 10% relative humidity difference characterised in that the liquid is viscous and contaings a hydroscopic material.

Suitable viscous liquids include polyurethanes, polyethylene glycols, propylene glycols, polyoxyethylene polyoxypropylene diol block copolymers which have the correct viscosity characteristics and are capable of deforming so as to distribute an applied pressure more or less evenly over their surface. Suitable polyurethane viscous liquids include those hydrophilic polyurethane gels described in International Application No. WO 82/01306 and European Patent Application No. 122035 which are incorporated hereinafter by cross reference.

Other suitable but more favoured viscous liquids include those made by materials such as polyvinyl alcohol, polyvinyl pyrolidone, polyacrylamide, polyethylene glycol, carboxymethylcellulose, cellulose and cellulosic derivatives, vegetable gums such as guar gum, gum agar which when added to a suitable liquid cause that liquid to become viscous.

Less preferred viscous liquids include non-aqueous viscous liquids made by the combination of a mineral oil and a gelling agent such as aluminium stearate or a silica such as Aerosil (Trade Mark), and gel emulsions containing an oil phase such as mineral oil, an emulsifier such as Brij 52 (Brij is a trade mark), a coupling agent such as plyethylene glycol 600, and water.

Suitably the viscosity (as measured at 39° C. using a Ferranti Shirley Cone and Plate Viscometer with a 1 cm radius cone and a 1200 g spring) of the viscous liquid will be between 500 and 25,000 Poise and preferably between 1,500 and 6,000 Poise.

Suitable hydroscopic materials for incorporation in the viscous liquid include inorganic materials such as anhydrous silica gel, anhydrous calcium chloride, anhydrous aluminium oxide and sodium bromide. Other suitable hygroscopic materials include organic compounds such as glycerol, glycerine and propylene glycol.

The viscous liquid together with the hydroscopic material when contained in a device will suitably absorb moisture vapour at a rate greater than 50 mg/72 hrs/cm$^2$ of the skin contacting surface of a device and will preferably absorbe moisture vapour at a rate greater than 150 mg/72 hrs/cm$^2$ of the skin contacting surface of a device.

Even when the hygroscopic material is included in an aqueous viscous liquid the resulting material when placed in a device will suitably be capable of absorbing moisture vapour at rates greater than 50 mg/72 hrs/cm$^2$ of the skin contacting surface of the device.

The viscous liquid containing a hygroscopic material and film forming the walls of the envelope and the adhesive when present are suitably all transparent so that the condition of the skin beneath the device may be monitored during the wearing period.

It is envisaged that once applied to the body the device can remain in position for a week or even longer. During this period the moisture produced by normal perspiration of the skin under the device must be removed otherwise the skin will become waterlogged and degenerate. Thus the moisture must be transmitted through the wall of the envelope and absorbed by the viscous liquid containing a hygroscopic material.

In both aspects of the present invention described hereinbefore suitable examples for the film which contacts the body of the wearer of the device are described in British Patent Specification No. 1280631 as backing materials, which are incorporated herein by cross-reference. Preferred polymers for forming the film are polyurethanes such as those known as Estane (Registered Trade Mark of B. F. Goodrich Ltd.) Suitable Estanes include Other preferred polymers for forming the film are polyetherester block copolymers such as Hytrel (Registered trade mark). Suitable Hytrels include Hytrel 4056. Yet other preferred polymers for forming the film are polyether polyamide block copolymers such as Pebax (Registered trade mark). Suitable Pebax include Pebax 2533 SN OO.

The thickness of the film employed in the device of this invention is chosen to produce the desired moisture vapour transmission rate (MVTR). Suitably the thickness of the film which will give the correct MVTR and be sufficiently strong to withstand the pressure applied to it will be in the range 25 to 100 microns. The film will be chosen so that its MVTR will be greater than 300 gm$^{-2}$24 hr$^{-1}$ and preferably will be greater than 500 gm$^{-2}$24 hr$^{-1}$, at 37° C. and at 100%–10% relative humidity.

For ease of manufacture it is convenient to form the envelope entirely of a moisture vapour permeable film. However, it is envisaged that the moisture absorbing viscous liquid may be retained between a moisture vapour permeable film which is to contact the skin of the wearer and a moisture vapour impermeable film. The moisture vapour impermeable film may be polyolefin, polyvinylchloride or the like.

In one embodiment of each of invention the surface of the device which is to contact the skin may carry an adhesive layer whereby the device may be adhered to the skin in use. By adhering the device to the skin it is less likely to be dislodged or moved out of place if the wearer moves or is moved or if the moisture absorbing viscous liquid is relatively stiff. Suitable adhesives must be compatible with the skin, that is they will be hypoallergenic. Suitable adhesives will be synthetic polymers or mixtures thereof. Such adhesives may be selected from those described in British Patent Specification No. 1280631 and European Patent Application No. 35399, both which are incorporated herein by cross-reference. Preferred adhesives are those which have a MVTR such that the adhesive together with the film which is in contact with the skin has a MVTR of greater than 300 gm$^{-2}$24 hr$^{-1}$ and more preferably greater than 500 gm$^{-2}$24 hr$^{-1}$ when measured at 30° C. and 100%–10% relative humidity. Suitable adhesives are those formed from polyacrylates or polyvinyl ethers.

Normally the adhesive will be applied to the film in the form of a continuous layer. However it is envisaged that the adhesive could be applied to form a discontinuous or a pattern spread layer. If desired the adhesive may incorporate an antibacterial agent such as a chlorhexidine salt.

In a further aspect the film which forms the body contacting layer may be extended to form a margin around the moisture absorbing viscous liquid filled envelope. The body contacting layer may carry an adhesive layer for sticking to the skin over the whole of its surface or only on the marginal portions. The adhesive layer may be continuous or discontinuous or a pattern spread layer.

The envelope may be formed by conventional means from the appropriate polymer film. Suitably the film may be formed into strips or shapes of the appropriate size, folded and heat sealed along two sides to provide an envelope with an opening or the envelopes may be blow moulded from suitable polymer.

Preferred embodiments of shaped devices of the present invention will now be described by way of example only and with reference to the accompanying drawing in which:

FIG. 1 shows a top view of a device suitably for application to the sacrum of a patient.

FIG. 1 shows a device with the flexible elastomeric envelope in the shape of a letter "U" (1) suitable for use around the sacrum of a patient. The two arms (2) of the flexible elastomeric envelope are separated by a gap (3) that is 5 cm wide. The width of each arm (2) is 7 cm as measured between the outer face (4) of the arm and the inner face (5) of the arm. The width of the base (5) of the flexible elastomeric envelope is 7 cm as measured from the outer face (6) of the base to the inner face (7) of the base. The overall length of the flexible elastomeric envelope is 15 cm as measured from the ends (8) of the arms to the outer face (6) of the base. The flexible elastomeric envelope is filled with a moisture absorbing viscous liquid to a thickness of 1 cm. The walls of the flexible elastomeric envelope are formed from a moisture vapour permeable polyurethane which is approximately 75 microns thick and is heat sealed around its edges to form the "U" shape.

The size of the device will vary depending upon the area of the body to which the device is to be applied. Some suitable devices are described in European Patent Application No. 122035 and U.S. Pat. No. 4516571 are incorporated hereinafter by cross-reference. Thus small size devices will be applied to the sacrum and heels. Larger devices will be used for application to the elbows and as cushions in wheel chairs whilst the largest devices will be used as mattresses. A small size device, in the form of a pad, will have dimensions of 10 cm by 10 cm (approximately). The thickness of the pad will be suitably 0.5 cm to 2.5 cm, more suitably 0.75 to 2.0 cm and preferably 1.0 to 1.5 cm, for example 1.4 cm. The amount of viscous liquid containing a hygroscopic material which is used will suitably be 50 to 250 ml, more suitably 75 to 200 ml and preferably 100 to 150 ml, for example 140 ml. The amount of viscous liquid containing a hygroscopic material required will depend upon the viscosity.

Where reference is made to moisture vapour transmission it is intended that such measurements are carried out by the Payne cup method which is described in the Description.

DESCRIPTION

Determination of moisture vapour transmission rates

Discs of the material under test are clampled over Payne Permeability Cups (flanged metal cups) using sealing rings and screw clamps., The exposed surface area of the test sample is 10 cm². Each cup contains approximately 10 ml of distilled water.

After weighing the cups are placed in a fan assisted electric oven which is maintained at 37°±1° C. The relative humidity within the oven is maintained at approximately 10% by placing 1 kg of anhydrous 3-8 calcium chloride on the floor of the oven.

The cups are removed after 24 hours, allowed to cool for 20 minutes and reweighed. The moisture vapour transmission rate of the test material is calculated from the weight loss and expressed in units of grams of weight per square meter per 24 hours.

EXAMPLE 1

Preparation of a device suitable for use on the heel

A viscous liquid was made by adding 30 gms polyvinyl alcohol (m.w. 29,400) grade GL05 to 100 gms water. To the resultant viscous liquid was added 100 gms sodium bromide.

A polyether polyamide copolymer film was extruded in the conventional manner using a melt temperature of approximately 185° C. The resultant film thickness was approximately 170 microns. This film was moulded into the appropriate shape using a vacuum mould. The shape chosen for the device for the heel is that described in EPO Application No. 122035. The average thickness of the film after vacuum moulding was approximately 75 microns.

A part of the viscous liquid containing the hygroscopic material prepared above (100 ml) was transferred to the larger of the two pouches of the polyether polyamide copolymer film and 25 ml of the viscous liquid containing the hygroscopic material prepared above was transferred to the smaller of the two pouches of the polyether polyamide copolymer film formed in the vacuum mould. A further piece of extruded polyether polyamide copolymer film with a thickness of 75 microns was then heat sealed to the viscous liquid filled pouches in such a manner as to exclude all the air from the two independent envelopes thus formed. The polyether polyamide copolymer film thus sealed to the viscous liquid containing the hygroscopic material filled pouches extended on all sides by 10 cm beyond these filled pouches. This extended area of polyether polyamide copolymer film was coated with a suitable pressure sensitive adhesive at a mass weight of 30 gsm. The adhesive face of the device was then placed onto a silicone release paper and the whole device sealed into a substantially water vapour impermeable bag for storage.

EXAMPLE 2

Preparation of a device suitable for use on the sacrum

A viscous liquid containing a hygroscopic material was made by dissolving 2 gms hydroxyethylcellulose (Natrosol 250 HH (Hercules Powder Co.)), 17 gms sodium chloride and 8.5 gms of glycerine in 72.5 mls water.

A polyurethane film was cast onto a silicone release paper at a weight of 60 gsm using a polyurethane syrup comprising 100 parts of Estane 5714F (available from B. F. Goodrich Ltd.), 5 parts of Gasil 23 fine silica (available from Crossfield Chemical Ltd.), 240 parts of tetrahydrofuran and 160 parts acetone. The resultant film was cut into strips so that on folding each strip in half and heat sealing the two edges, an envelope approximately 10 cm by 10 cm was formed.

A part of the viscous liquid containing the hygroscopic material prepared above (140 ml) was transferred to the polyurethane envelope and the envelope closed by heat sealing along the fourth edge.

The resultant pad 10 cm by 10 cm and 1.4 cm thick was suitable for use to prevent formation of pressure sores on the sacrum.

EXAMPLE 3

Preparation of a device suitable for use on the heel

A linear polyurethane gel was prepared from the following:
Random polyoxyethylene polyoxypropylene diol copolymer (Breox 75 W270)(Mol. wt. 2,600): 2,600 g
Polypropylene glycol (Mol. wt. 1,025): 1,025 g
Irganox 1010: 39.4 g
4,4'Dicyclohexylmethane diisocyanate: 314 g
di-n-butyl tin laurate (catalyst): 0.8 g The first four ingredients were mixed together to form a homogeneous mixture whilst warming to 60° C. The catalyst was then added with stirring. The resultant homogeneous reaction mixture was poured into a mould and cured in an oven at 90° C. for 2 hours. The resultant hydrophylic polyurethane was obtained as a viscous liquid. To 130 gms of this viscous liquid was added a 100 gms sodium bromide.

A polyetherester block copolymer film was extruded in the conventional manner using a melt temperature of approximately 185° C. The resultant film thickness was approximately 170 microns. This film was then moulded into the appropriate shape using a vacuum mould. The appropriate shape for a device for the heel is that shown and described in European Patent Application No. 122035. The average thickness of the film after vacuum moulding was approximately 75 microns.

A part of the viscous liquid containing the hygroscopic material prepared above (100 ml) was transferred to the larger of the two pouches of the polyetherester block copolymer film and 25 ml of the viscous liquid containing the hygroscopic material prepared above was transferred to the smaller of the two pouches of the polyetherester block copolymer film formed in the vacuum mould. A further piece of extruded polyetherester block copolymer film with a thickness of 75 microns was then heat sealed to the viscous liquid containing the hygroscopic material filled pouches in such a manner as to exclude all the air from th two independent envelopes thus formed. The polyetherester block copolymer film thus sealed to the viscous liquid containing the hygroscopic material filled pouches extended on all sides by 10 cm beyond the viscous liquid containing the hygroscopic material filled envelopes. This extended area of polyetherester block copolymer block was coated with a suitable pressure sensitive adhesive at a mass weight of 30 gsm. The adhesive face of the devices was then placed onto a silicone release paper and the whole device sealed into a substantially water vapour impermeable bag for storage.

EXAMPLE 4

A device suitable for use on the sacrum

A polyether polyamide block copolymer film was extruded in a conventional manner using a melt temperature of approximately 185° C. The resultant film thickness was approximately 170 microns. This film was moulded into the appropriate shape using a vacuum mould. The average thickness of the film after vacuum moulding was approximately 75 microns.

The following description of the device is made with reference to FIG. 1 and the description thereof.

The device was formed in the shape of a "U" where the arms (2) of the device were approximately 4 cms apart and the arms (2) were each approximately 5 cms wide. The base (5) of the "U" shaped device was approximately 5 cms wide. The length of the device from the top (8) of the arm to the bottom (6) of the base was approximately 13 cms.

A moisture absorbing viscous liquid was prepared by adding 30 gms of polyvinyl alcohol (m.w. 29,400) grade GL05 and 100 gms sodium bromide to 100 gms of water. A 100 mls of the moisture absorbing viscous liquid was then transferred to the device formed from the polyether polyamide film in the vacuum mould. A further piece of extruded polyether polyamide copolymer film with a thickness of 75 microns was then heat sealed to the moisture absorbing viscous liquid filled device in such a manner as to exclude all the air from the envelope thus formed. The polyether polyamide copolymer film thus sealed to the moisture absorbing viscous liquid filled device extended on all sides by 10 cm beyond the moisture absorbing viscous liquid filled envelope. This extended area of polyether polyamide film was coated with a suitable pressure sensitive adhesive at a mass weight of 30 gsm. The adhesive fce of the device was then placed onto a silicone release paper and the whole device sealed into a substantially vapour impermeable bag for storage.

EXAMPLE 5

A film of polyether ester block copolymer (Hytrel 4056) was formed in the conventional manner by extrusion to provide a film of thickness of approximately 170 $\mu m$. This film was then moulded into the 'U' shaped device as defined hereinbefore and described in Example 4.

The mould was filled with the hydrophilic polyurethane gel described in Example 3. A further piece of extruded polyether ester block copolymer film of thickness 75 $\mu m$ was heat sealed to the hydrophilic gel-filled mould in a manner so as to exclude all the air from the envelope thus formed. This latter film extended beyond the U-shaped envelope of the device by about 10 cm. This extended area of Hytrel film was coated with a polyacrylate ester copolymer adhesive at a weight per unit area of 30 gsm. The adhesive facer of the device was then placed onto a silicone release paper. A keyhole shaped section was removed from between the arm of the 'U'-shaped device so that the device when applied to the sacrum would not interfere with natural bodily functions.

We claim:

1. A device for the prophylaxis of pressure sores which comprises a liquid retained within a flexible elastomeric envelope having a body contacting surface, wherein the body contacting surface of the device is a film having a moisture vapour transmission rate of greater than 300 gm$^{-2}$24 h$^{-1}$ at 37° C. at 100% to 10% relative humidity difference, the liquid is viscous and absorbs moisture vapour and is capable of deforming so as to distribute an applied pressure from the body contacting the surface evenly over the surface of the device and the flexible elastomeric envelope is formed in the shape of the letter "U".

2. A device as claiming in claim 1 in which the flexible elastomeric envelope in the shape of the letter 'U' between 5 cm and 30 cm long, between 5 cm and 40 cm wide, and each arm of the device is suitably between 1 cm and 10 cm wide and the two arms are separated by a gap which has a width of 1 cm to 10 cm.

3. A device as claimed in claim 2 in which the flexible elastomeric envelope is in the shape of the letter 'U' is between 10 and 20 cm long, 12 and 26 cm wide and each arm is between 2 cm and 6 cm wide.

4. A device for the prophylaxis of pressure sores which comprises a liquid retained within a flexible elastomeric envelope in the shape of the letter "U" having a body contacting surface, wherein the body contacting surface of the device is a film having a moisture vapour transmission rate of greater than 300 gm$^{-2}$24 h$^{-1}$ at 37° C. at 100% to 10% relative humidity difference, the liquid is a viscous liquid which absorbs moisture vapour and which contains a hygroscopic material.

5. A device as claimed in claim 4 in which the viscous liquid is an aqueous solution of polyvinyl alcohol and the hygroscopic material is sodium bromide.

6. A device for the prophylaxis of pressure sores which comprises a liquid retained within a flexible, elastomeric envelope in which the body contacting surface of the device is a film having a moisture vapour transmission rate of greater than 300 gm$^{-2}$24 hr$^{-1}$ at 37° C. at 100% to 10% relative humidity difference characterised in that the liquid is viscous and contains a hygroscopic material.

7. A device as claimed in claim 6 in which the viscous liquid together with the hygroscopic material when contained in the device absorbs moisture vapour at a rate greater than 50 mg/72 hr/cm$^2$ of the skin contacting surface of the device.

8. A device as claimed in either of claim 6 in which the hygroscopic material is an inorganic material selected from the group consisting of anhydrous silica gel, anhydrous calcium chloride, anhydrous aluminium oxide and sodium bromide.

9. A device as claimed in claim 6 in which the viscous liquid has a viscosity of between 1500 and 6000 Poise when measured at 39° C. using a Ferranti-Shirley Core and Plate Viscometer with a 1 cm radius core and a 1200 g spring.

10. A device as claimed in claim 6 in which the viscous liquid is an aqueous solution of a polymer selected from the group consisting of polyvinyl alcohol, polyvinyl pyrrolidone, polyacrylamide, polyethylene glycol, carboxymethyl cellulose, cellulose derivatives and vegetable gums.

11. A device as claimed in claim 6 in which the viscous liquid is selected from the group consisting of polyurethane, polyethylene glycol, propylene glycol and polyoxyethylene polyoxypropylene diol block copolymers.

12. A device as claimed in claim 6 in which the viscous liquid is an aqueous solution of polyvinyl alcohol and the hygroscope material is sodium bromide.

13. A device as claimed in claim 1 in which the body contacting surface of the device carries an adhesive layer.

14. A device as claimed in claim 1 in which the body contacting surface is a polyether ester block copolymer.

15. A device as claimed in claim 1 in which the flexible elastomeric envelope contains from 50 to 250 ml of viscous liquid.

16. A device as claimed in either of claims 1 or 6 in which the device has thickness of from 0.5 to 3.0 cm.

17. A device as claimed in claim 6, in which the body contacting surface of the device carries an adhesive layer.

18. A device as claimed in claim 6, in which the body contacting surface is a polyether ester block copolymer.

19. A device as claimed in claim 6, in which the flexible elastomeric envelope contains from 50 to 250 ml of viscous liquid.

20. A device as claimed in claim 6, in which the device has a thickness of from 0.5 to 3.0 cm.

* * * * *